US011350499B2

(12) United States Patent
Jung et al.

(10) Patent No.: US 11,350,499 B2
(45) Date of Patent: May 31, 2022

(54) SYSTEMS AND METHODS FOR CONTROLLED ILLUMINATION OF LIGHT-EMITTING DIODES

(71) Applicant: Alcon Inc., Fribourg (CH)

(72) Inventors: David Jung, Tustin, CA (US); Jason L. Lee, Anaheim, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/192,951

(22) Filed: Mar. 5, 2021

(65) Prior Publication Data

US 2021/0289600 A1    Sep. 16, 2021

Related U.S. Application Data

(60) Provisional application No. 62/987,617, filed on Mar. 10, 2020.

(51) Int. Cl.
| | | |
|---|---|---|
| *H05B 45/34* | (2020.01) | |
| *H05B 45/36* | (2020.01) | |
| *H05B 47/19* | (2020.01) | |
| *H05B 45/345* | (2020.01) | |
| *H05B 45/325* | (2020.01) | |
| *A61F 9/007* | (2006.01) | |

(52) U.S. Cl.
CPC ............ *H05B 45/34* (2020.01); *A61F 9/007* (2013.01); *H05B 45/325* (2020.01); *H05B 45/345* (2020.01); *H05B 45/36* (2020.01); *H05B 47/19* (2020.01)

(58) Field of Classification Search
CPC ........ H05B 45/10; H05B 45/20; H05B 45/34; H05B 45/37; H05B 45/52
See application file for complete search history.

(56) References Cited

U.S. PATENT DOCUMENTS

| | | | |
|---|---|---|---|
| 7,443,296 B2 | 10/2008 | Mezhinsky | |
| 7,551,077 B2 | 6/2009 | Raybuck et al. | |
| 9,931,447 B2 | 4/2018 | Layser | |
| 2002/0145041 A1* | 10/2002 | Muthu | H05B 45/46 235/454 |
| 2007/0257860 A1* | 11/2007 | Langer | H05B 45/20 345/46 |
| 2010/0181507 A1* | 7/2010 | Maruyama | H04N 1/02865 250/552 |
| 2011/0109243 A1 | 5/2011 | Kim et al. | |
| 2011/0204778 A1 | 8/2011 | Sadwick et al. | |

(Continued)

*Primary Examiner* — Tung X Le

(57) ABSTRACT

Systems and methods are disclosed for controlled illumination of LEDs. An example system comprises: a plurality of LEDs; an LED controller; a current buffer adapted to receive an input bias level signal from the LED controller, wherein a set of LEDs to be controlled together are connected in parallel with each other in a circuit with the current buffer; and at least one current limiting resistor connected in the circuit with the plurality of LEDs and the current buffer. The systems and methods are adapted to control the illumination of the LEDs by applying a constant voltage to the circuit based upon the input bias level signal, thereby controlling the illumination of the light-emitting diodes without the use of pulse width modulation. Crosstalk interference with RFID components due to pulse width modulation is thereby avoided.

10 Claims, 3 Drawing Sheets

(56) References Cited

U.S. PATENT DOCUMENTS

| | | | |
|---|---|---|---|
| 2013/0063042 A1* | 3/2013 | Bora | H05B 45/20 |
| | | | 315/292 |
| 2017/0170727 A1* | 6/2017 | Mizuno | H05B 45/3725 |
| 2018/0035516 A1* | 2/2018 | Dobai | H04B 5/0031 |
| 2018/0376566 A1* | 12/2018 | Newton | H05B 47/18 |
| 2019/0081563 A1 | 3/2019 | Yang et al. | |
| 2019/0110862 A1 | 4/2019 | Anderson | |
| 2020/0187930 A1* | 6/2020 | Zacharia | A61B 90/30 |

* cited by examiner

SYSTEMS AND METHODS FOR CONTROLLED ILLUMINATION OF LIGHT-EMITTING DIODES

TECHNICAL FIELD

This disclosure is directed to systems and methods for controlled illumination of light-emitting diodes (LEDs).

BACKGROUND

Various ways of controlling illumination of LEDs have been implemented for various applications. In series control, for example, a number of LEDs are connected in series and driven by a single LED driver. The setup is simple; however, a high voltage may be needed, and if one LED in the array fails, the whole set fails.

In another example, individual LEDs are controlled separately with individual channels using a multi-channel LED driver. While this arrangement allows individualized control, control signals to separate channels may have a time delay, which can result in time delays in illumination of different LEDs that are intended to be illuminated simultaneously.

LED illumination has been used, for example, in ophthalmic surgical systems. LED illumination has been used to indicate the status of instrument ports, indicating, for example, whether an instrument port is available for an instrument to be connected, whether an instrument is properly connected to the instrument port, whether a properly-connected instrument is available for use, etc. Example systems for instrument identification and associated illumination are described and shown in U.S. Pat. Nos. 7,443,296 and 7,551,077, the entire disclosures of which are incorporated herein by reference. Such systems may use radio frequency identification (RFID) tags in the instruments with RFID antennas at the instrument ports. The connection status can be determined from the RFID tag and then indicated with the LEDs.

In some prior systems, the LEDs are controlled using pulse width modulation. However, pulse width modulation can cause crosstalk interference between the LED driving circuit and an RFID antenna in proximity to the LED driving circuit. Higher order harmonics of the pulse width modulation signal can affect the RFID signal, since the RFID components are located close to the LED circuitry.

Accordingly, there is a continuing need for improved systems and methods for controlled illumination of LEDs.

SUMMARY

The present disclosure is directed to improved systems and methods for controlled illumination of LEDs.

In some example embodiments, an instrument identification system for an ophthalmic surgical system comprises: a RFID antenna; a plurality of LEDs; a light-emitting diode controller; a current buffer connected to the light-emitting diode controller and adapted to receive an input bias level signal from the light-emitting diode controller, wherein the LEDs in the plurality of LEDs are connected in parallel with each other in a circuit with the current buffer; and at least one current limiting resistor connected in the circuit with the plurality of LEDs and the current buffer; wherein the system is adapted to control the illumination of the LEDs by applying a constant voltage to the circuit based upon the input bias level signal, thereby controlling the illumination of the light-emitting diodes without the use of pulse width modulation.

In some example embodiments, the LEDs in the plurality of LEDs may be arranged in a ring. The RFID antenna may be circular. The LEDs in the plurality of LEDs may be arranged in a ring around the RFID antenna. The light-emitting diode controller may comprise a digital to analog converter.

In some example embodiments, the system comprises multiple circuits of LEDs, with the LEDs in a circuit connected in parallel with each other. A system may comprise one, two, three, or more such circuits of LEDs. In one example, a first plurality of LEDs in a first circuit may emit a first color, a second plurality of LEDs in a second circuit may emit a second color, and a third plurality of LEDs in a third circuit may emit a third color. For example, the first, second, and third colors may be red, green, and blue, respectively.

In some example embodiments, each light-emitting diode has at least one dedicated current limiting resistor connected in series with that light-emitting diode and connected in parallel with the remaining LEDs in the same circuit. In some example embodiments, at least one current limiting resistor is connected in series with all of the LEDs in the same circuit.

In some example embodiments, a system for controlled illumination of LEDs comprises: a plurality of LEDs; a light-emitting diode controller; a current buffer connected to the light-emitting diode controller and adapted to receive an input bias level signal from the light-emitting diode controller, wherein the LEDs in the plurality of LEDs are connected in parallel with each other in a circuit with the current buffer; and at least one current limiting resistor connected in the circuit with the plurality of LEDs and the current buffer; wherein the system is adapted to control the illumination of the LEDs without the use of pulse width modulation.

In some example embodiments, a method for controlled illumination of LEDs comprises: sending an input bias level signal from a light-emitting diode controller to a current buffer; and, based on the input bias level signal, providing a constant bias voltage level to a circuit comprising a plurality of LEDs, wherein the LEDs in the circuit are connected in parallel with each other.

The above examples and other examples will be understood by persons having ordinary skill in the art based on this disclosure.

BRIEF DESCRIPTION OF THE DRAWINGS

The accompanying drawings illustrate examples of the systems and methods disclosed herein and, together with the description, serve to explain the principles of the disclosure.

Figure 1:
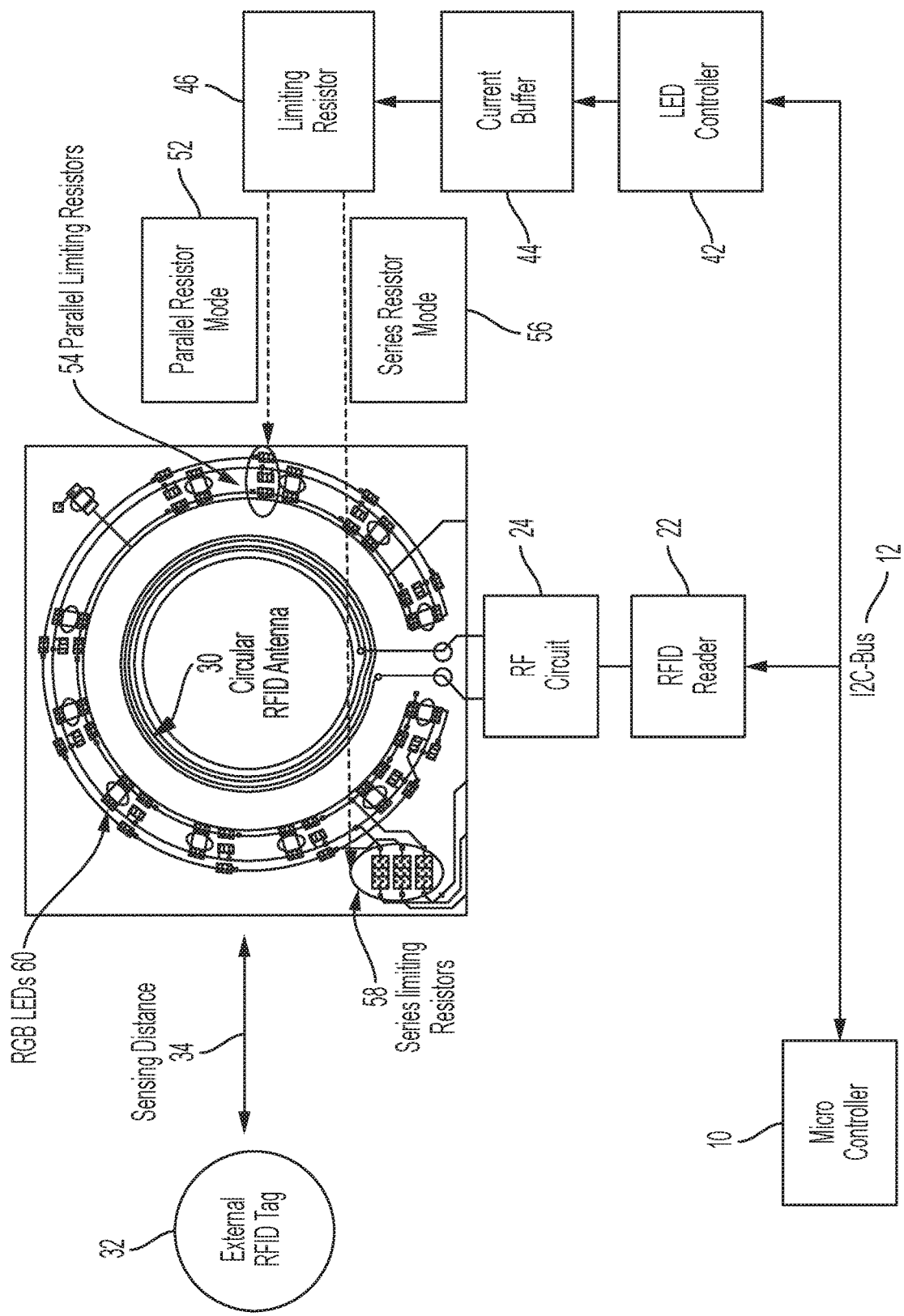
FIG. 1 is a block diagram illustrating components of an example system in accordance with the disclosure.

The accompanying drawings may be better understood by reference to the following detailed description.

DETAILED DESCRIPTION

For the purposes of explaining the principles of the disclosure, reference is made to the drawings, and specific language is used to describe the same. It will nevertheless be understood that, by reference to certain examples, no limitation of the scope of the disclosure is intended. Any alterations and further modifications to the described example systems, devices, instruments, and methods, and any further application of the principles of the disclosure, are fully contemplated as would normally occur to one skilled in the art to which the disclosure relates. In particular, the features, components, and/or steps described with respect to one example of the disclosure may be combined with features, components, and/or steps described with respect to other examples of the disclosure and may be modified and/or substituted as would normally occur to one skilled in the art. For simplicity, in some instances the same reference numbers may be used in the drawings to refer to the same or like parts.

FIG. 1 is a block diagram illustrating components of an example system in accordance with the disclosure. The system may be implemented, for example, as an instrument identification system for an ophthalmic surgical system, which may be used for ophthalmic surgical procedures such as cataract surgery and/or retinal surgery. Except for differences as described herein, the ophthalmic surgical system may be similar to ophthalmic surgical systems as shown and described in U.S. Pat. No. 9,931,447, the disclosure of which is hereby incorporated by reference herein in its entirety, and/or to ophthalmic surgical systems that have been known and used, such as the CENTURION® Vision System available from Alcon Laboratories, Inc. (Fort Worth, Tex.) or the CONSTELLATION® Vision System available from Alcon Laboratories, Inc. (Fort Worth, Tex.), or any other ophthalmic surgical system suitable for use with the principles described herein.

The ophthalmic surgical system may include an ophthalmic surgical console that houses a computer system and components for one or more ophthalmic surgical functions, a display screen, one or more external controls such as a footswitch, and a plurality of instruments that may be connected to the ophthalmic surgical console. The ophthalmic surgical console may have a fluidics cassette dock to which a fluidics cassette may be installed.

The instruments that may be connected to the ophthalmic surgical console may be for any of a variety of functions useful in ophthalmic procedures. For example, such instruments may include one or more phacoemulsification instruments (e.g., for removal of cataractous lenses), diathermy instruments, vitrectomy instruments, laser therapy instruments, illumination instruments, cutters, forceps, scissors, or any other type of instruments suitable for use in ophthalmic procedures.

The ophthalmic surgical console may have one or more instrument ports to which the instruments may be connected. Each instrument port may be configured for a specific type of instrument.

The instruments to be connected to the ophthalmic surgical console may have connectors for connecting with the appropriate instrument ports. The instrument connectors may have machine-readable information which can be read by a reader of the ophthalmic surgical console when an instrument is connected to an instrument port. For example, each instrument may have a radio-frequency identification (RFID) tag, and each instrument port of the ophthalmic surgical console may have an associated RFID antenna for reading the RFID tags of connected instruments. Each instrument port of the ophthalmic surgical console also may have an indicator, such as a ring of light-emitting diodes (LEDs), for indicating the status of a particular port and/or instrument. For example, different colors or modes (e.g., solid or blinking) for the LEDs could be used to indicate whether an instrument port is available for an instrument to be connected, whether an instrument is properly connected to the instrument port, whether a properly-connected instrument is available for use, etc. Example systems for instrument identification and associated illumination are described and shown in U.S. Pat. Nos. 7,443,296 and 7,551,077, the disclosures of which are hereby incorporated by reference herein in their entirety.

In FIG. 1, an RFID tag of an instrument to be connected to an ophthalmic surgical console is represented as external RFID tag 32. The remaining elements of FIG. 1 can be implemented within the ophthalmic surgical console itself.

A microcontroller 10 may be used to control the operations of RFID tag reading and LED illumination. For reading an RFID tag 32 of an instrument connected to an instrument port of the ophthalmic surgical console, the microcontroller 10 may communicate over an I2C bus 12 with an RFID reader 22. As instructed by the microcontroller 10, the RFID reader 22 sends RFID discovery signals through an RF circuit 24 and an RFID antenna 30 to read any connected external RFID tag 32. The RFID antenna 30 is located at the instrument port adjacent to where an external RFID tag 32 of an instrument would be located when the instrument is connected to the instrument port. The external RFID tag 32 of the instrument is within sensing distance of the RFID antenna when the instrument is connected to the instrument port. The sensing distance may be, for example, about 10 mm to about 50 mm, and can be varied with RF power of the RFID reader 22 and/or the design of the RFID antenna 30 or the RFID tag 32.

When the RFID reader 22 detects an external RFID tag, the information from the RFID tag is read by the RFID reader 22. The information is communicated to the microcontroller 10.

The microcontroller 10 receives and verifies the external RFID tag information and then, based on the information, sends one or more control commands to an associated LED controller 42 for appropriate illumination of the LEDs to indicate the status of the instrument port and/or the instrument. The microcontroller 10 may communicate over I2C bus 12 with the LED controller 42. The LED controller 42 may comprises a digital to analog converter (DAC).

For illuminating the desired LEDs, the LED controller 42 sends a control voltage as an input bias level signal to the current buffer 44. The current buffer 44 may comprise a high current op-amp. The current buffer 44 receives the input bias level signal from the LED controller 42 and serves as a buffer to sink current from parallel LEDs, as described in more detail below and in conjunction with FIGS. 2 and 3.

A plurality of LEDs 60 are connected in a circuit with the current buffer 44. At least one current limiting resistor 46 is connected in the circuit with the plurality of LEDs 60 and the current buffer 44. In the illustrated example, red-green-blue (RGB) LEDs 60 are used. A single RGB LED 60 may in fact comprise three LEDs: a red LED, a green LED, and a blue LED. In the illustrated example, a plurality of red LEDs are connected together in a first circuit with the current buffer 44; a plurality of green LEDs are connected together in a second circuit with the current buffer 44; and a plurality of blue LEDs are connected together in a third circuit with the current buffer 44. Other colors and sets of LEDs are possible.

In the illustrated example, the RGB LEDs 60 are arranged in a ring. The RFID antenna 30 may be circular, and the RGB LEDs 60 may be arranged in a ring around the RFID antenna 30.

Figure 2:
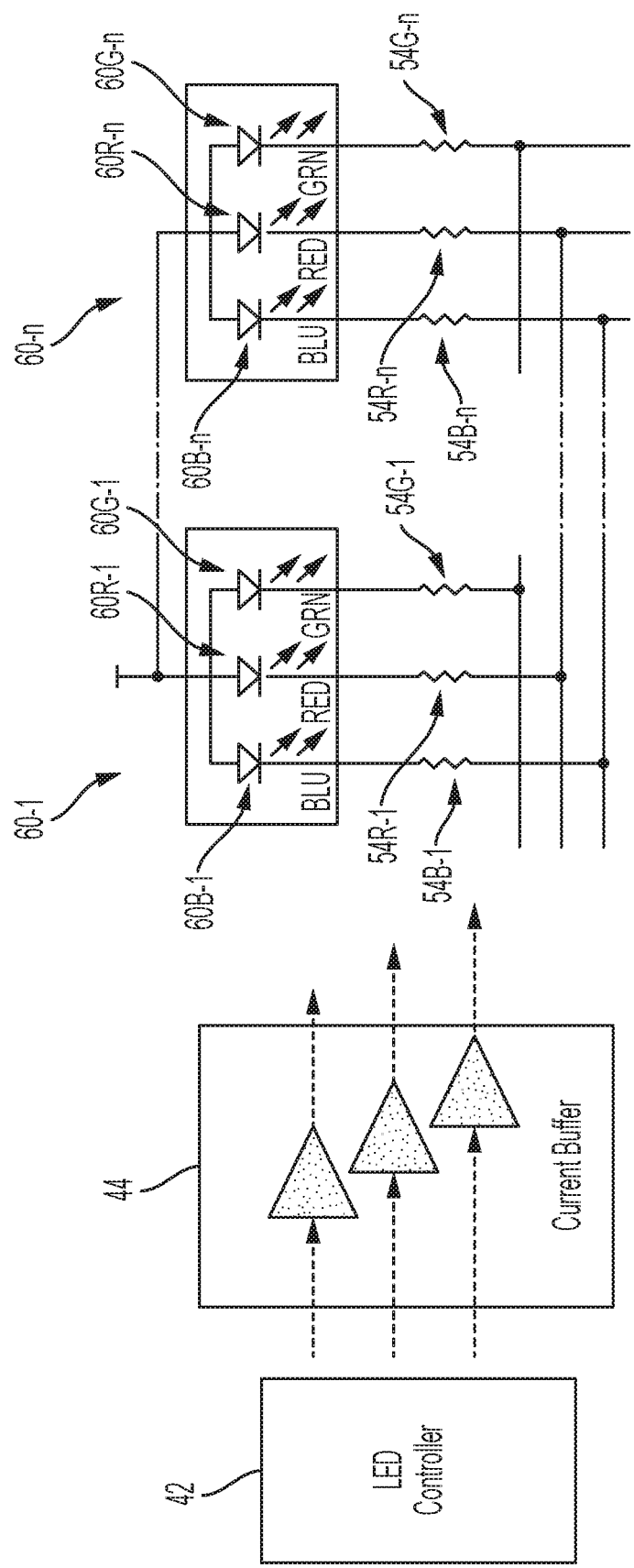
FIG. 2 is a schematic diagram illustrating components of an example system in accordance with the disclosure.
Figure 3:
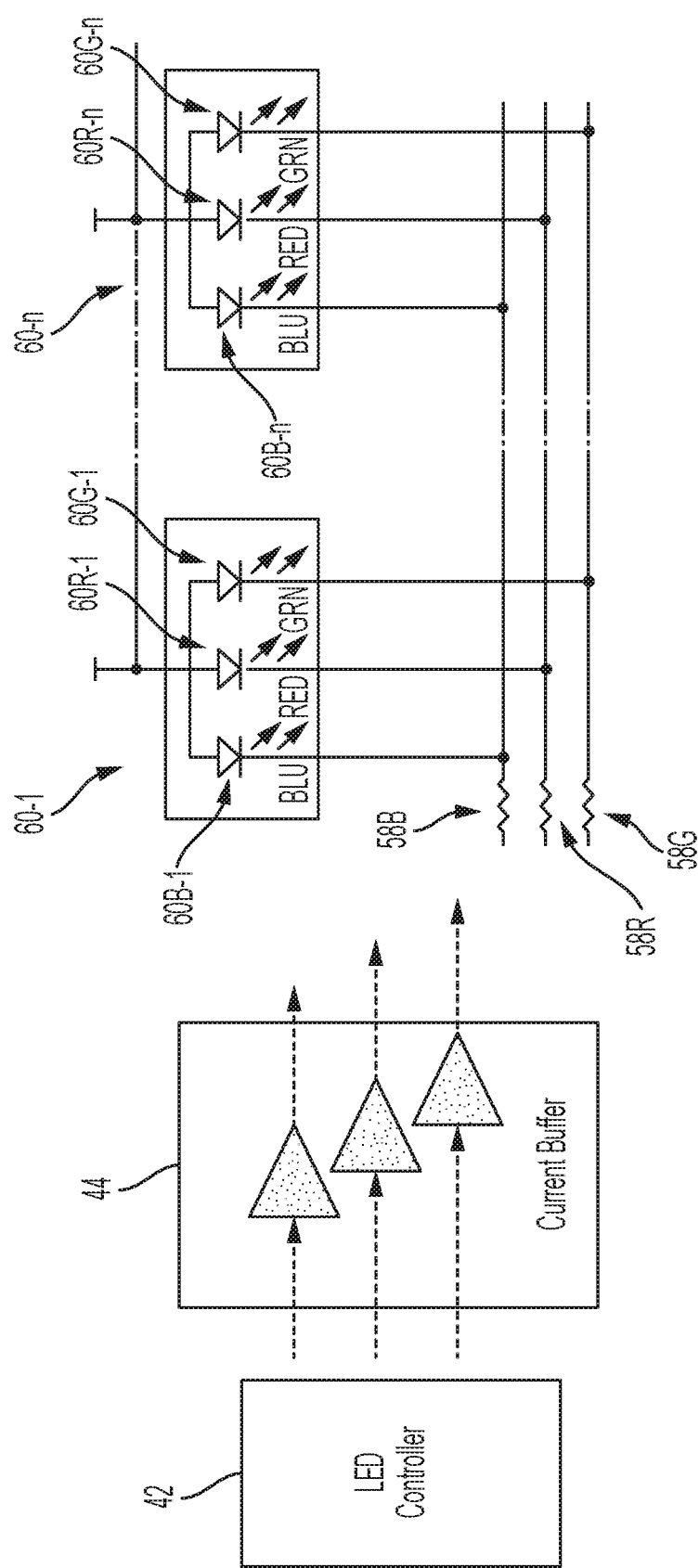
FIG. 3 is a schematic diagram illustrating components of another example system in accordance with the disclosure.

In each circuit of LEDs, the LEDs in the circuit are connected in parallel with each other. As illustrated in FIGS. 2 and 3, the LEDs may be connected with current limiting resistors in multiple ways. Two ways are illustrated together in FIG. 1, although it will be understood by persons skilled in the art that only one of the two ways need be used.

In a first example, designated in FIG. 1 as parallel resistor mode 52, each LED has at least one dedicated current limiting resistor 54 connected in series with that LED and connected in parallel with the remaining LEDs in the same circuit. This is illustrated schematically in FIG. 2.

FIG. 2 is a schematic diagram illustrating components of an example system in accordance with the disclosure. A plurality of RGB LEDs 60 are used together in any suitable number. The designations -1 through -n are used in the drawings to indicate the first through the nth item of a set of items. In the example illustrated in FIG. 2, a plurality of red LEDs 60R-1 through 60R-n are connected together in a first circuit with the current buffer 44; a plurality of green LEDs 60G-1 through 60G-n are connected together in a second circuit with the current buffer 44; and a plurality of blue LEDs 60B-1 through 60B-n are connected together in a third circuit with the current buffer 44.

In the example of FIG. 2, each LED has at least one dedicated current limiting resistor connected in series with that LED and connected in parallel with the remaining LEDs in the same circuit. Each red LED 60R has at least one dedicated current limiting resistor 54R connected in series with that red LED 60R and connected in parallel with the remaining red LEDs in the same circuit. For example, red LED 60R-1 has a dedicated current limiting resistor 54R-1 connected in series with it and connected in parallel with the remaining red LEDs in the same circuit, while red LED 60R-n has a dedicated current limiting resistor 54R-n connected in series with it and connected in parallel with the remaining red LEDs in the same circuit. Each green LED 60G has at least one dedicated current limiting resistor 54G connected in series with that green LED 60G and connected in parallel with the remaining green LEDs in the same circuit. For example, green LED 60G-1 has a dedicated current limiting resistor 54G-1 connected in series with it and connected in parallel with the remaining green LEDs in the same circuit, while green LED 60G-n has a dedicated current limiting resistor 54G-n connected in series with it and connected in parallel with the remaining green LEDs in the same circuit. Each blue LED 60B has at least one dedicated current limiting resistor 54B connected in series with that blue LED 60B and connected in parallel with the remaining blue LEDs in the same circuit. For example, blue LED 60B-1 has a dedicated current limiting resistor 54B-1 connected in series with it and connected in parallel with the remaining blue LEDs in the same circuit, while blue LED 60B-n has a dedicated current limiting resistor 54B-n connected in series with it and connected in parallel with the remaining blue LEDs in the same circuit.

In a second example, designated in FIG. 1 as series resistor mode 56, at least one current limiting resistor 58 is connected in series with all of the LEDs in a circuit. This is illustrated schematically in FIG. 3.

FIG. 3 is a schematic diagram illustrating components of another example system in accordance with the disclosure. As in FIG. 2, a plurality of RGB LEDs 60 are used together in any suitable number, and the designations -1 through -n are used to indicate the first through the nth item of a set of items. Similar to the example in FIG. 2, in the example illustrated in FIG. 3, a plurality of red LEDs 60R-1 through 60R-n are connected together in a first circuit with the current buffer 44; a plurality of green LEDs 60G-1 through 60G-n are connected together in a second circuit with the current buffer 44; and a plurality of blue LEDs 60B-1 through 60B-n are connected together in a third circuit with the current buffer 44.

In the example of FIG. 3, at least one current limiting resistor is connected in series with all of the LEDs in a circuit. Each circuit of red LEDs 60R-1 through 60R-n has at least one current limiting resistor 58R connected in series with all of the LEDs in that circuit. Each circuit of green LEDs 60G-1 through 60G-n has at least one current limiting resistor 58G connected in series with all of the LEDs in that circuit. Each circuit of blue LEDs 60B-1 through 60B-n has at least one current limiting resistor 58B connected in series with all of the LEDs in that circuit.

The current limiting resistors may be selected depending on the LED forward voltage. In an example, the forward voltage for a red LED is 2.0 V, and the forward voltage for a green or blue LED is 3.1 V. The limiting resistance is related to LED forward voltage according to the following formula:

$$R(\text{Limiting Resistance}) = (V_s(\text{Supply Voltage}) - V_f(\text{LED Forward Voltage}))/\text{Current}$$

In use, the LED controller 42 sends an input bias level signal to the current buffer 44. The current buffer 44 receives the input bias level signal from the LED controller 42. Based on the input bias level signal, a constant voltage is applied to a circuit comprising a plurality of LEDs, for example a circuit of a single color of LEDs. The current buffer 44 serves as a buffer to sink current from the parallel LEDs in the circuit.

Persons having ordinary skill in the art will recognize that systems and methods as disclosed herein have one or more advantages over prior approaches. For example, in comparison with prior approaches, systems and methods as disclosed herein are adapted to control the illumination of the LEDs without the use of pulse width modulation. Among LED driving and dimming methods, some of them such as pulse width modulation can cause crosstalk between the LED driving circuit and an RFID antenna in proximity to the LED driving circuit. Higher order harmonics of the pulse width modulation signal can affect the RFID signal, since the RFID components are located close to the LED circuitry. Persons having ordinary skill in the art will recognize that systems and methods as disclosed herein are adapted to control the illumination of the LEDs without the use of pulse width modulation and consequently without the crosstalk and interference that can be associated with pulse width modulation.

In addition, persons having ordinary skill in the art will recognize that systems and methods as disclosed herein provide a simple and efficient controlling scheme of LED brightness with linear control. Traditional DACs may have a current limit around 10 mA to 20 mA per port. This is not enough to take the high current sink needed for multiple LEDs arranged in parallel. Typical indicator LEDs have forward currents of 20 mA to 25 mA each. With multiple LEDs arranged in parallel, a current sink need can be around 100 mA to 200 mA. As disclosed herein, a current buffer provides a high current sink to facilitate illumination of multiple LEDs without pulse width modulation. LEDs in a single circuit can be illuminated simultaneously and efficiently.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. An instrument identification system for an ophthalmic surgical system, the instrument identification system comprising:
    a radio frequency identification antenna;
    a plurality of light-emitting diodes;
    a light-emitting diode controller;
    an RFID reader coupled to the radio frequency identification antenna;
    a microcontroller coupled to the light-emitting diode controller and the RFID reader, the microcontroller programmed to receive and verify information from the RFID reader, the microcontroller further programmed to send a control command to the light-emitting diode controller based on the received and verified information;
    a current buffer connected to the light-emitting diode controller and adapted to receive an input bias level signal from the light-emitting diode controller, wherein the plurality of light-emitting diodes are connected in parallel with each other in a circuit with the current buffer; and
    at least one current limiting resistor connected in the circuit with the plurality of light-emitting diodes and the current buffer;
    wherein the system is adapted to control the illumination of the light-emitting diodes by applying a constant voltage to the circuit based upon the input bias level signal, thereby controlling the illumination of the light-emitting diodes without the use of pulse width modulation.

2. The instrument identification system for an ophthalmic surgical system as in claim 1, wherein the radio frequency identification antenna is circular.

3. The instrument identification system for an ophthalmic surgical system as in claim 1, wherein the light-emitting diodes in the plurality of light-emitting diodes are arranged in a ring around the radio frequency identification antenna.

4. The instrument identification system for an ophthalmic surgical system as in claim 1, wherein the light-emitting diode controller comprises a digital to analog converter.

5. The instrument identification system for an ophthalmic surgical system as in claim 1, wherein the plurality of light-emitting diodes connected in parallel with each other in the circuit is a first plurality of light-emitting diodes connected in a first circuit, and
    wherein the system further comprises a second plurality of light-emitting diodes connected in parallel with each other in a second circuit.

6. The instrument identification system for an ophthalmic surgical system as in claim 5, further comprising a third plurality of light-emitting diodes connected in parallel with each other in a third circuit.

7. The instrument identification system for an ophthalmic surgical system as in claim 6, wherein the first plurality of light-emitting diodes emit a first color, the second plurality of light-emitting diodes emit a second color, and the third plurality of light-emitting diodes emit a third color.

8. The instrument identification system for an ophthalmic surgical system as in claim 7, wherein the first color is red, the second color is green, and the third color is blue.

9. The instrument identification system for an ophthalmic surgical system as in claim 1, wherein the at least one current limiting resistor comprises a plurality of current limiting resistors, wherein each light-emitting diode has at least one dedicated current limiting resistor connected in series with that light-emitting diode and connected in parallel with the remaining light-emitting diodes in the same circuit.

10. The instrument identification system for an ophthalmic surgical system as in claim 1, wherein the at least one current limiting resistor comprises at least one current limiting resistor connected in series with all of the light-emitting diodes in the plurality of light-emitting diodes.

* * * * *